United States Patent
Trozera (10) Patent No.: US 6,780,261 B2
(45) Date of Patent: Aug. 24, 2004

(54) METHOD OF MANUFACTURING AN IMPLANTABLE STENT HAVING IMPROVED MECHANICAL PROPERTIES

(75) Inventor: Thomas Trozera, Del Mar, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 85 days.

(21) Appl. No.: 10/185,838

(22) Filed: Jun. 27, 2002

(65) Prior Publication Data

US 2004/0000361 A1 Jan. 1, 2004

(51) Int. Cl.[7] .................................................. C21D 8/10
(52) U.S. Cl. ....................... 148/593; 148/590; 148/592; 148/597; 148/598; 148/608
(58) Field of Search .............................. 148/590, 592, 148/593, 597, 598, 608, 603, 419

(56) References Cited

U.S. PATENT DOCUMENTS

| | | |
|---|---|---|
| 5,630,840 A | 5/1997 | Mayer |
| 5,718,159 A | 2/1998 | Thompson |
| 5,824,077 A | 10/1998 | Mayer |
| 6,086,773 A | 7/2000 | Dufresne et al. |
| 6,200,685 B1 | 3/2001 | Davidson |
| 6,248,190 B1 | 6/2001 | Stinson |

FOREIGN PATENT DOCUMENTS

| | | | |
|---|---|---|---|
| JP | 408176744 | * 7/1996 | ........... C22C/38/00 |
| JP | 10204530 | 8/1998 | |

OTHER PUBLICATIONS

International Search Report from PCT/US 03/20212.

* cited by examiner

Primary Examiner—Deborah Yee
(74) Attorney, Agent, or Firm—Fish & Richardson, P.C.

(57) ABSTRACT

A metallurgical process for producing a metallic implantable medical device, such as a stent, in a condition wherein the metallic alloy of the device has improved mechanical properties. The starting material is formed into an oversized tube which is drawn to finished outer diameter. The drawing process cold works the tube to produce a material having a high dislocation density and a yield strength that is above approximately 125 ksi. Next, the drawn tube is heat treated at a temperature of approximately one-half the absolute melting temperature of the alloy. The heat treatment causes dislocations to rearrange, forming sub-grains and re-crystallization of the grain structure. Upon cooling, a material is obtained having a yield strength between approximately 45–70 ksi and an elongation exceeding 40 percent. The material also has good resistance to fatigue fracture due to the fine grains and sub-grains that are established during the heat treatment.

25 Claims, 6 Drawing Sheets

METHOD OF MANUFACTURING AN IMPLANTABLE STENT HAVING IMPROVED MECHANICAL PROPERTIES

FIELD OF THE INVENTION

The present invention pertains generally to a metallurgical process for manufacturing an implantable medical device. More particularly, the present invention pertains to a process for producing an improved intravascular medical device, such as a stent, which has improved grain structure in the alloy of the stent which provides improved fatigue and corrosion resistance while maintaining ductility for expansion and strength upon expansion.

BACKGROUND OF THE INVENTION

Stents are often prescribed to treat arteries that have been blocked or narrowed by atherosclerosis. A stent generally includes a tubular metallic structure that is delivered to the site of the blockage on the balloon of a balloon catheter. With the stent located at the desired position in the artery, the balloon is inflated to expand the diameter of the stent, lodging the stent in the wall of the artery. The balloon can then be deflated and removed from the body. After balloon removal, the stent remains in the artery to maintain a passageway for blood flow through the artery. The wall thickness of the tubular stent is generally made as thin as possible to provide a large passageway for blood flow through the artery.

From a design perspective, the material used to fabricate a stent preferably has good ductility to allow the stent to be expanded by the balloon without fracturing the stent. The stent material preferably also has good strength to ensure that the stent maintains its shape to keep the artery open. Furthermore, during the service life of a stent, the stent is exposed to cyclic stresses from the constant pressure cycling in the artery due to the beating of the heart. Thus, it is important to fabricate the stent from a material having good resistance to fatigue failure. In addition to these mechanical property requirements, the stent materials are preferably chemically stable, corrosion resistant and biocompatible.

Heretofore, stainless steel has been used in the fabrication of stents. In terms of biocompatibility, this material has a substantial history of successful application in invasive medical devices with little or no unacceptable biological response. Table 1 shows the composition range of a particular type of stainless steel (UNS S31673).

TABLE 1

Chemical Requirements, Heat Analysis

| ELEMENT | COMPOSITION, % |
|---|---|
| Carbon | 0.030 max |
| Manganese | 2.00 max |
| Phosphorus | 0.025 max |
| Sulfur | 0.010 max |
| Silicon | 0.75 max |
| Chromium[A] | 17.00 to 19.00 |
| Nickel | 13.00 to 15.00 |
| Molybdenum[A] | 2.25 to 3.00 |
| Nitrogen | 0.10 max |
| Copper | 0.50 max |
| Iron[B] | balance |

[A]The compositional requirement shall meet the following: % Cr + 3.3 X % Mo ≥ 26.0
[B]Approximately equal to the difference between 100% and the sum percentage of the other specified elements. The percentage Iron content by difference is not required to be reported.

A metallurgical process to prepare a stent from type UNS S31673 typically begins with the manufacture of an oversized tube. Next, the oversized tube is annealed at a temperature of approximately 1050 degrees C., leaving the tube in a very soft condition. After annealing, the tube is drawn to the final tube diameter required for the unexpanded stent. This drawing process cold works the steel to a fixed amount, providing the strength required to use the steel in stent applications. This process results in a material having a yield strength in the range of 40–60 ksi and an elongation in the range of 25–40 percent. Alternatively, stents are fabricated from fully annealed stainless steel that has a yield strength between 35–45 ksi and elongation about 50%. The grain size of material manufactured by the above methods is typically between 30–200 grains per $10^{-4}$ square inch. Although these properties are somewhat satisfactory for relatively thick-walled stents, by improving the mechanical properties (including fatigue resistance) of stent materials, thinner, more reliable stents can be employed.

As previously stated, a material used to make a stent must be formable (i.e., have sufficient ductility and weldability to be formed into the appropriate final stent shape), and yet needs to provide good mechanical properties in the finished stent to hold the lumen open. Stainless steel and alloys, such as the radiopaque alloys disclosed in U.S. patent application Ser. No. 10/112,391, filed Mar. 28, 2002, entitled "Platinum Enhanced Alloy and Intravascular or Implantable Medical Devices Manufactured Therefrom" (the disclosure of which is incorporated herein by reference), are readily formable, can be strengthened by work hardening, and exhibit good mechanical properties in finished stents. Furthermore, these alloys are readily weldable due to low carbon content. As for biocompatibility, the alloys have a successful history in invasive medical device applications. However, it would be beneficial to utilize improved manufacturing techniques that maintain the above properties while also improving corrosion resistance and reducing the likelihood of fatigue fracture, especially in thin-walled stents.

SUMMARY OF THE INVENTION

The present invention is directed to a method for producing a metallic medical device having improved mechanical properties. The process is particularly useful for manufacture of implantable medical devices and/or intravascular medical devices. The alloy used is preferably stainless steel or an enhanced radiopaque alloy as disclosed in U.S. patent application Ser. No. 10/112,391, filed Mar. 28, 2002, entitled "Platinum Enhanced Alloy and Intravascular or Implantable Medical Devices Manufactured Therefrom." A preferred medical device of the present invention includes a stent which is a generally tubular structure having an exterior surface defined by a plurality of interconnected struts having interstitial spaces therebetween. The generally tubular structure is expandable from a first position, wherein the stent is sized for intravascular insertion, to a second position, wherein at least a portion of the exterior surface of the stent contacts the vessel wall. The expanding of the stent is accommodated by flexing and bending of the interconnected struts throughout the generally tubular structure.

The present invention includes a preferred metallurgical process for producing an implantable medical device, such as a stent, in a condition wherein the alloy of the stent has improved mechanical properties. For the present invention, the starting material is preferably a stainless steel, such as UNS S31673. The starting material can also include a platinum enhanced alloy as previously cited. In the starting material, the levels of carbon and other interstitial elements such as nitrogen and oxygen are controlled below a predetermined amount to reduce the occurrence of grain boundary precipitates during the metallurgical process. In preferred embodiments, carbon and oxygen are controlled to below 0.03 and 0.02 weight percent, respectively.

In accordance with preferred embodiments of the present invention, the starting material is cold worked to produce a material having a high dislocation density and a yield strength that is above approximately 125 ksi. Generally, to obtain this cold worked state, the starting material is deformed to a strain of approximately 30–55 percent. In manufacturing a stent, this step is accomplished by beginning with an oversized tube which is first drawn to about the final diameter of the unexpanded stent. The strain that occurs during tube drawing is generally sufficient to cold work the material. Furthermore, because of the thin-walled nature of the tube, uniform strains are imparted throughout the tube during the drawing process, leading to a stent having uniform properties.

Next, the cold-worked material is heat treated at a temperature of approximately $0.5T_M$, where $T_M$ is the absolute melting temperature of the alloy. In preferred embodiments, heat treatment is conducted between $0.4T_M$ and $0.6T_M$. During this heat treatment, self diffusion is enabled and vacancies become mobile. This allows dislocations to rearrange and form cells of dislocations (i.e., sub-grains), as well as re-crystallization of the material grain structure. Because the levels of carbon and the other interstitial elements are controlled below a predetermined amount, unwanted grain boundary precipitates are reduced (e.g., minimized) during the heat treatment. Further, because of the thin-walled nature of the stent, heat treatment can be accomplished quickly. For a stent of wall thickness 0.005 inch, heat treatment is completed in about 30 to 40 minutes.

Upon cooling, a material is obtained having a yield strength between about 40–65 ksi and an elongation exceeding 40 percent. The resultant material also has good corrosion resistance due to the reduction of grain boundary precipitates. Furthermore, the sub-grains and re-crystallized grain structure that are established during the heat treatment provide improved fatigue resistance. Unlike prior manufacturing processes, cold working after heat treatment to improve the mechanical properties of the stent is not necessary.

DETAILED DESCRIPTION OF THE INVENTION

The present invention is directed to a process for manufacturing metallic articles. The process is particularly useful in the manufacture of implantable and/or intravascular medical devices wherein improved fatigue failure resistance and improved corrosion resistance are desired. The preferred method of manufacture is detailed herein. First, however, one preferred implantable medical device is described, a stent. It is, however, recognized that the present alloy could be utilized in any medical device wherein improved mechanical properties discussed herein are desired.

Figure 1A:
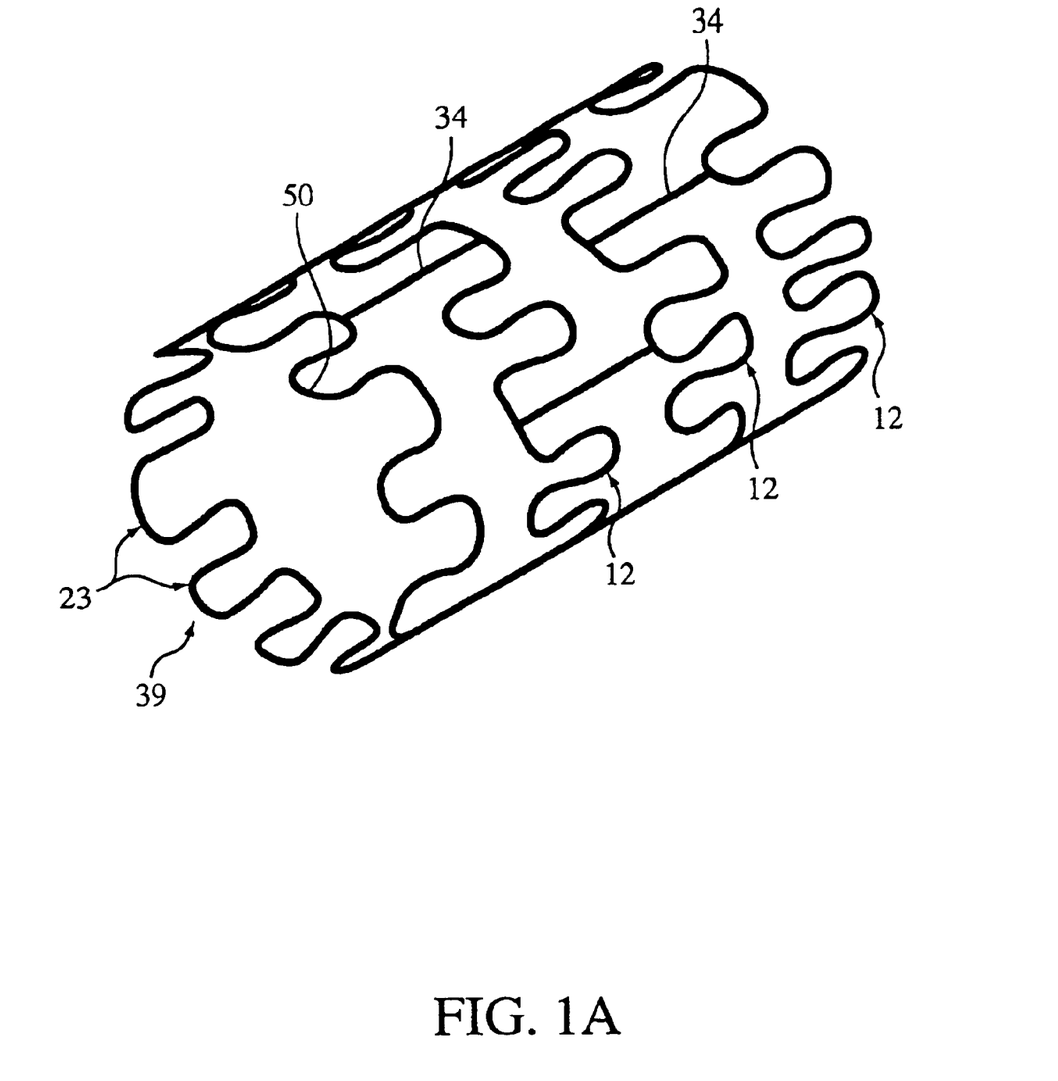
FIG. 1A is a perspective view of a preferred stent of the present invention.

Referring now to the drawings, wherein like references refer to like elements throughout the several views, FIG. 1A shows a perspective view of a stent 39 in accordance with a preferred product manufactured according to the process of the present invention. The stent generally comprises a plurality of radially expandable cylindrical elements 12 disposed generally co-axially and interconnected by elements 34 disposed between adjacent expandable elements. The stent can be balloon expandable, self-expanding or a combination thereof. Within the cylindrical elements 12 are a series of struts or loops 50 of the stent 39. There are a series of open spaces between the struts or loops 50. This combination provides a preferred stent configuration. The cylindrical elements 12 are radially expandable due to their formation as a number of loop alterations or undulations 23 which resemble a serpentine pattern. The interconnecting elements 34 between adjacent radially expandable elements 12 are placed to achieve maximum flexibility for a stent. In the stent of FIG. 1A, the stent 39 has two interconnecting elements 34 between adjacent radially expandable cylindrical elements 12 which are approximately 180 degrees apart. The next pairing of interconnecting elements 13 on one side of a cylindrical element 12 is offset by 90 degrees from the adjacent pair. This alternation of interconnecting elements results in a stent which is longitudinally flexible in essentially all directions. Other configurations for placement of interconnecting elements are possible within the scope of the present invention. However, all of the interconnecting elements of an individual stent should be secured to either the peaks or valleys of the alternating loop elements in order to prevent shortening of the stent during expansion thereof and all of the radially facing struts will have one of the specifically designed configurations.

Figure 1B:
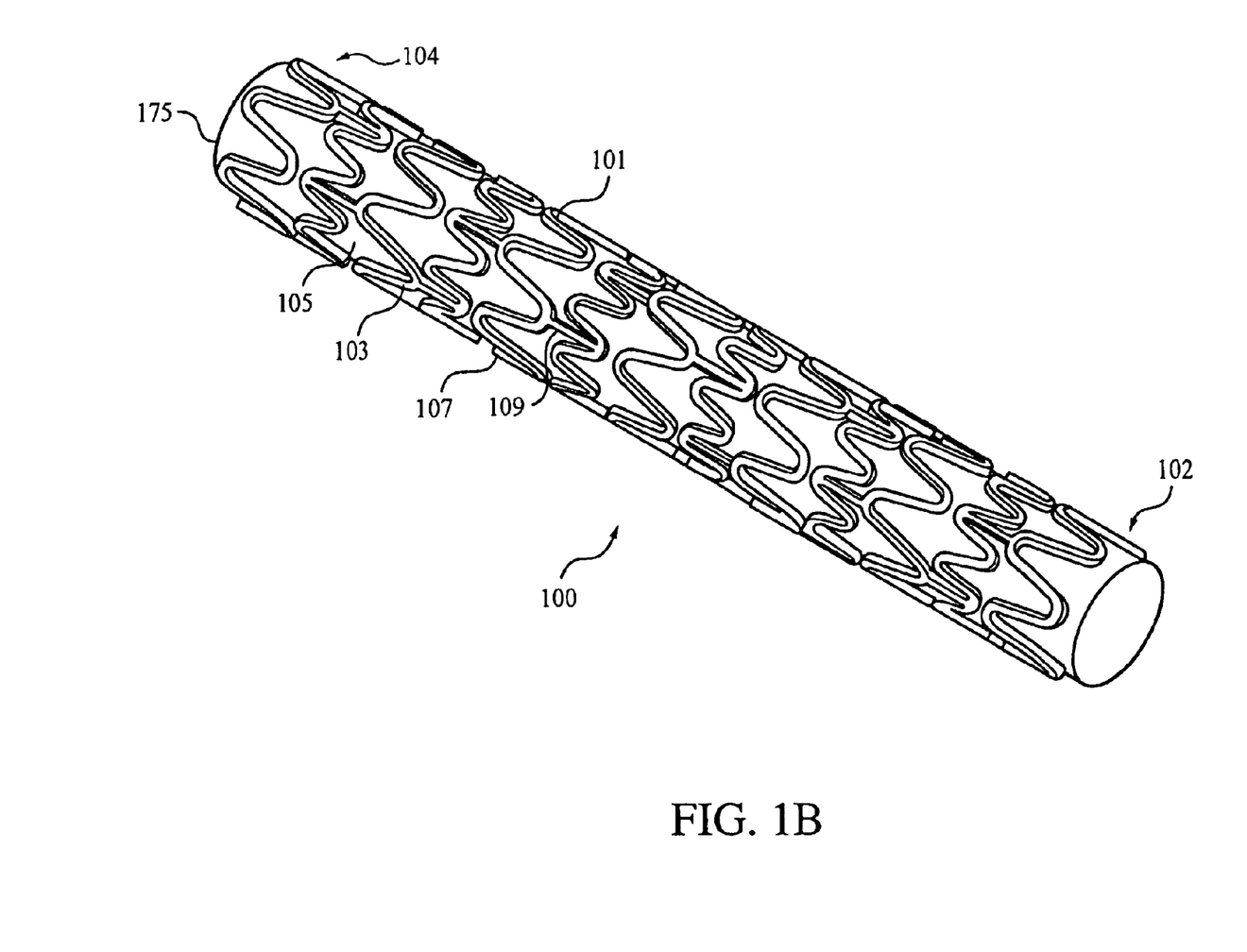
FIG. 1B is a perspective view of an alternative stent of the present invention in a non-expanded form as mounted over a mandrel.

Referring now to FIG. 1B, a perspective view of an alternative stent 100, in a non-expanded form mounted on a mandrel 175, manufactured in accordance with the present invention is depicted. The stent depicted in FIG. 1B is one alternative representative embodiment in which the method disclosed herein may be utilized. The skeletal frame of the stent 100 preferably includes struts 101 forming a distinct, repetitive pattern. This repetitive pattern consists of multiple U-shaped curves 103. These U-shaped curves 103 form interstitial spaces 105. The U-shaped curves 103 form elements 107 which are arranged along the longitudinal axis of the stent 100 so that the U-shaped curves 103 of abutting elements 107 may be joined through interconnecting elements 109. Through the interconnecting elements 109, a continuous framework is created between multiple elements 107 forming the stent 100.

Figure 2:
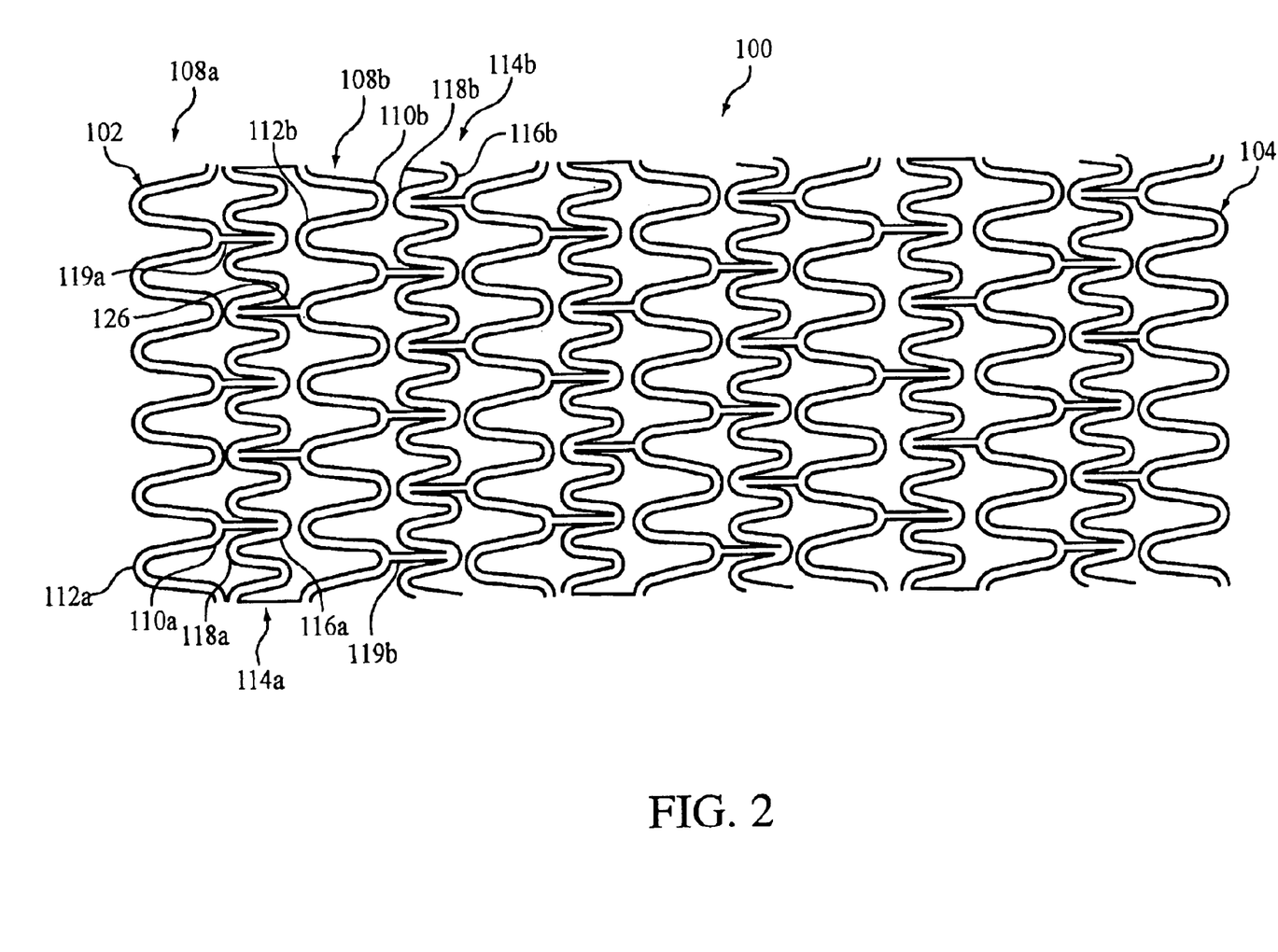
FIG. 2 is a plan view of the stent of FIG. 1B, detailing the skeletal frame structure of a preferred stent.

The stent of FIG. 1B is depicted in planar view in FIG. 2 so that the struts 101 and the framework they form can be described in more detail for preferred embodiments. Stent 100 has a proximal end 102, a distal end 104 and a flow path therethrough along a longitudinal axis 106. Stent 100 comprises a first undulating band 108a comprising a series of alternating first peaks 110a and first troughs 112a. First peaks 110a are oriented in a distal direction, and first troughs 112a are oriented in a proximal direction. First undulating band 108a is characterized by a first wavelength and a first amplitude.

Stent 100 further comprises a second undulating band 114a comprising a series of alternating second peaks 116a in a distal direction, and second troughs 118a which are oriented in a proximal direction. Second undulating band 114a is characterized by a second wavelength and a second amplitude. The second amplitude is different from the first amplitude, and the second wavelength is different from the first wavelength.

A plurality of longitudinally oriented first connectors 119a extend between first peaks 110a and second peaks 116a. Second peaks 116a, from which connectors extend, optionally have an enlarged outer radius as compared to second peaks from which no connectors extend.

Stent 100 further comprises a third undulating band 108b comprising a series of alternating third peaks 110b and third troughs 112b, and a fourth undulating band 114b comprising alternating fourth peaks 116b and fourth troughs 118b. Third peaks 110b and fourth peaks 116b are oriented in the distal direction, and third troughs 112b and fourth troughs 118b are oriented in the proximal direction. The third undulating band has a third wavelength and a third amplitude. Desirably, the third wavelength is equal to the first wavelength and the third amplitude is equal to the first amplitude. More desirably, the third band is identical in structure to the first band, as shown in FIG. 2. A plurality of longitudinally oriented second connectors 126 extend between second troughs 118a and third troughs 112b. Second troughs, from which connectors extend, optionally have an enlarged outer radius relative to second troughs from which no connectors extend. The fourth undulating band has a fourth wavelength and a fourth amplitude. Desirably, the fourth wavelength is equal to the second wavelength and the fourth amplitude is equal to the second amplitude. More desirably, the fourth band is identical in structure to the second band, as shown in FIG. 2. A plurality of longitudinally oriented third connectors 119b extend between third peaks 110b and fourth peaks 116b. Additional undulating bands may be present in the stent. Desirably, as shown in FIG. 2, the undulating bands of the stent alternate between first undulating bands of the first wavelength and first amplitude and second undulating bands of the second wavelength and second amplitude. Other arrangements of undulating bands are also within the scope of the invention.

The rigidity of the stents in the expanded state may be controlled by suitably arranging the connecting members. For example, where a stent with rigid ends and a more flexible middle portion is desired, more connecting members may be provided at the ends. Similarly, a stent with more flexible ends may be achieved by providing fewer connectors at the ends. A stent with increasing rigidity along its length may be provided by increasing the number of connectors along the length of the stent or by providing increasingly rigid undulating bands.

Figure 3:
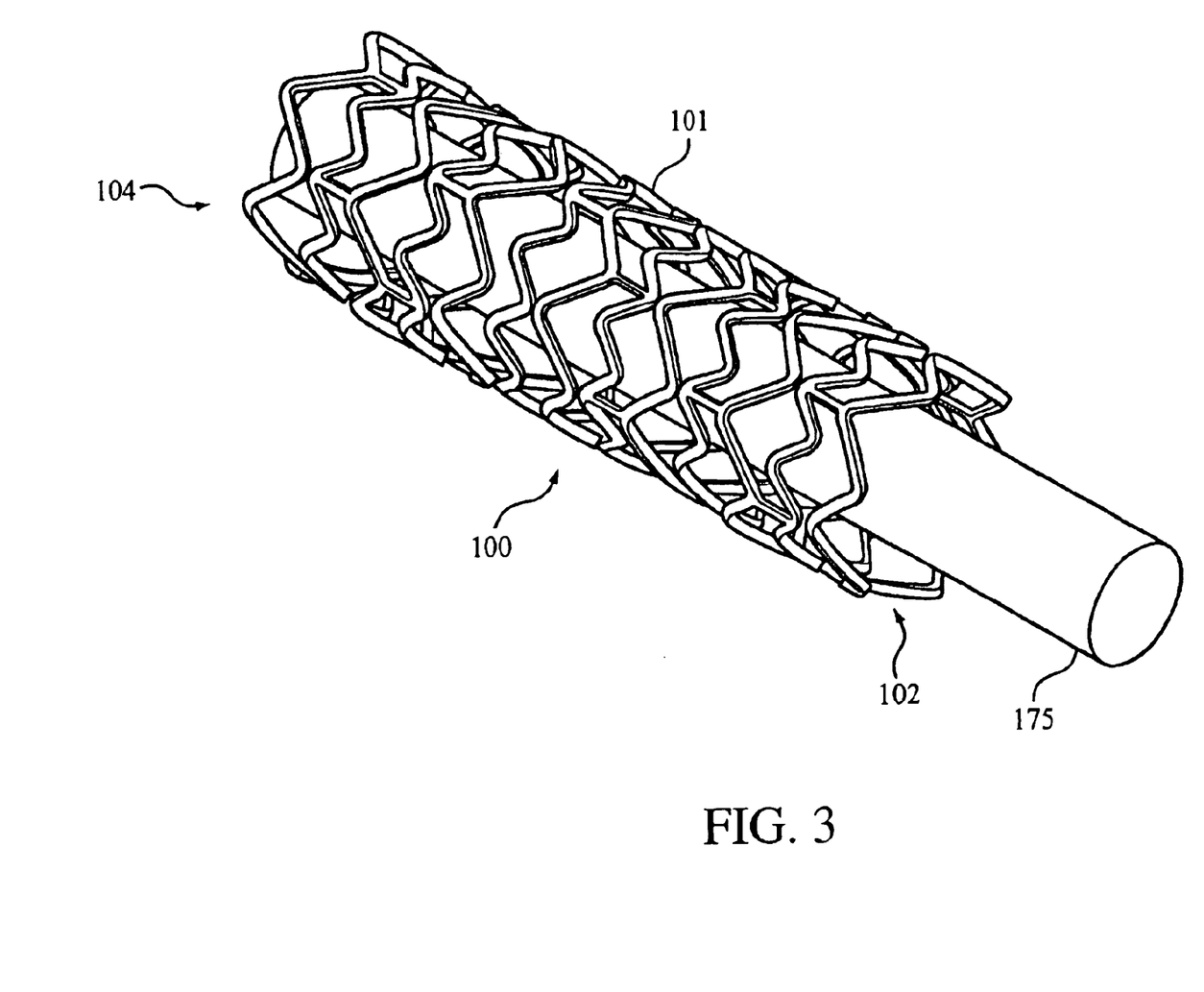
FIG. 3 is a perspective view of the stent of FIG. 1B in an expanded state with the mandrel shown to indicate expansion.

The stent of FIG. 1B is shown in an expanded state in FIG. 3. Bending of the struts accommodate expansion of the stent 100, with the final expanded structure resisting collapse of the lumen, when implanted, due to structural properties of the alloy of construction.

Preferred manufacturing methods of the present invention produce stents having improved mechanical properties. These mechanical properties are, in large part, due to the grain structure of the alloy of the final stent product resulting in part from no cold working subsequent to heat treatment.

In preferred embodiments of the present invention, the stent is manufactured from a thin-walled tube, which is then laser cut to provide the desired configuration. The tube may also be chemically etched or electrical discharge machined (EDM) to form the desired configuration. In an alternative embodiment, the stent may be made from a flat pattern which is then formed into a tubular shape by rolling the pattern so as to bring the edges together. The edges may then be joined as by welding or the like to provide a desired tubular configuration.

In preferred methods of the present invention, a metallic alloy is selected as a starting material. A preferred alloy is a stainless steel alloy, or alternatively, a platinum enhanced alloy as disclosed in U.S. patent application Ser. No. 10/112,391, filed Mar. 28, 2002, entitled "Platinum Enhanced Alloy and Intravascular or Implantable Medical Devices Manufactured Therefrom." In preferred alloys, the level of carbon is below 0.03% and the level of oxygen is controlled below 0.02% to reduce the occurrence of grain boundary precipitates during the processing. An oversized tube is first manufactured. The tube may be formed from a flat alloy material which is rolled and welded at the seam or alternative processes may be utilized. The oversized tube is then drawn to about the final diameter of an unexpanded stent during which process the strain which occurs is sufficient to cold work the material. The material thus has a high dislocation density and a yield strength that is greater than about 125 ksi. This strain is controlled to approximately 30% or more in a drawn tube. The strained material is then heated at a temperature of approximately $0.5T_M$, where $T_M$ is the absolute melting temperature of the alloy. In preferred embodiments, the heat treatment is conducted between about $0.4T_M$ and about $0.6T_M$. The heat treatment process allows dislocations to rearrange and form cells of dislocations or sub-grains and causes re-crystallization of the grain structure.

Figure 4:
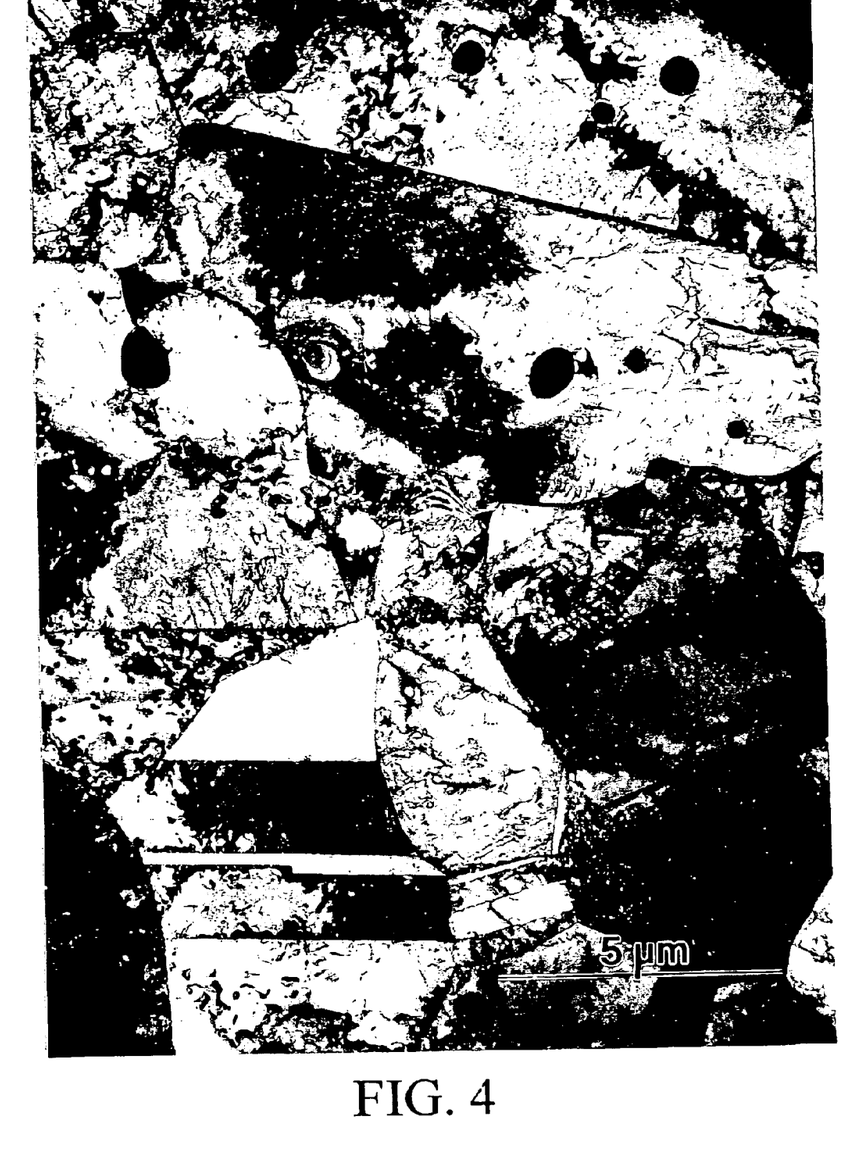
FIG. 4 is a photomicrograph taken using transmission electron microscopy (TEM) of the stainless steel material processed in accordance with the present invention showing dislocations arranged in cellular networks (i.e., sub-grains)
Figure 5:
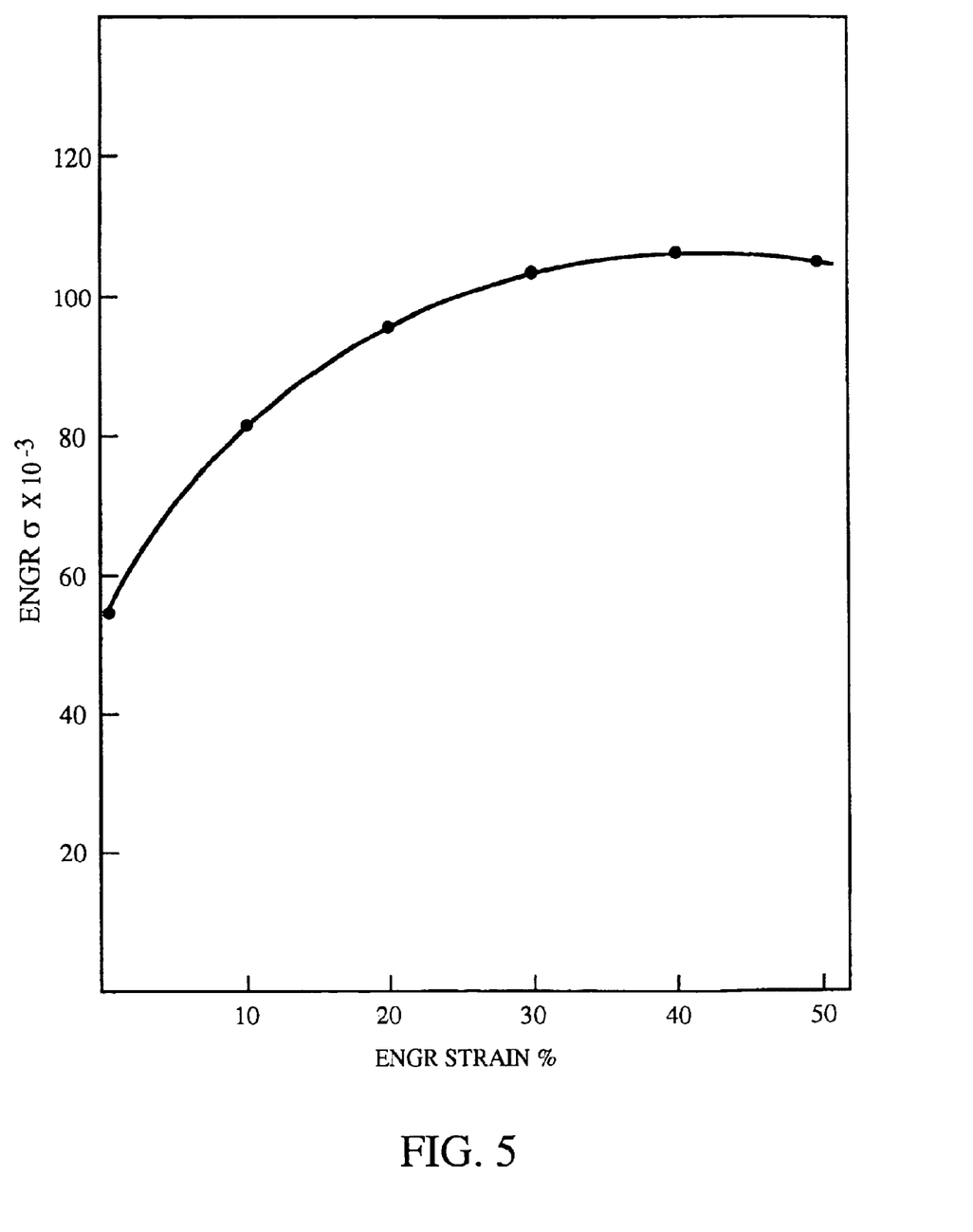
FIG. 5 is a true stress—true strain curve of the stainless steel material processed in accordance with the present invention.

A tube for a stent was manufactured from flat stock of UNS S31673 stainless steel having a thickness of approximately 0.006 inches. The flat stock was rolled into a 0.2-inch outside diameter tube. The seam of the tube was laser welded. The tube was then drawn to a final outside diameter of 0.060 inches with an attendant reduction in wall thickness from 0.006 inches to 0.0052 inches. Next, the drawn tube was heat treated in a vacuum furnace at an approximate temperature of 800 degrees Celsius for approximately 30 minutes. During the heat treatment, fine grains as well as sub-grains were formed as shown in the TEM photomicrograph of FIG. 4. Portions of the tube were then cut into three-inch lengths and pulled in tension. FIG. 5 shows the resulting true stress—true strain curve that was obtained. As shown, the material had a yield strength of approximately 55 ksi, an ultimate tensile strength of approximately 106 ksi and an elongation of approximately 50 percent. The material contained approximately 2000 grains per $10^{-4}$ square inch.

Those skilled in the art will recognize that the present invention may be manifested in a variety of forms other than the specific embodiments described herein. Accordingly, departures in form and detail may be made without departing from the scope and spirit of the present invention as described in the appended claims.

What is claimed is:

1. A process for manufacturing a stent assembly having improved mechanical properties, the process comprising the steps of:

first, providing an oversized tubular member of an alloy;

second, drawing the oversized tubular member to a smaller outer diameter and thinner wall to the tube to a yield strength above approximately 125 ksi; and third, heating the cold-worked tube to a first temperature for a sufficient time, followed by cooling to produce a material having a yield strength between about 40 ksi and about 70 ksi, and an elongation above 40 percent.

2. The process as recited in claim 1, wherein the first temperature is about one-half the absolute melting temperature of said alloy.

3. The process as recited in claim 1, wherein the first temperature is between about 40 percent of the absolute melting temperature to about 60 percent of the absolute melting temperature.

4. The process as recited in claim 1, wherein the alloy has less than about 0.03 weight percent carbon.

5. The process as recited in claim 4, wherein the alloy has less than approximately 0.02 weight percent oxygen and less than approximately 0.1 weight percent nitrogen.

6. The process of claim 1, wherein the alloy is a material comprising between approximately 17 and approximately 19 weight percent chromium and between approximately 13 and approximately 15 weight percent nickel.

7. The process as recited in claim 1, wherein the heat treated material has sub-grains and more than approximately 200 grains per $10^{-4}$ square inch.

8. A method for manufacturing a stent, said method comprising the steps of:
deforming a stainless steel having between approximately 17 and approximately 19 weight percent chromium and between approximately 13 and approximately 15 weight percent nickel to a strain in excess of approximately 30 percent; and
heating said deformed stainless steel to a first temperature, followed by cooling to produce a material having a yield strength between approximately 50 and approximately 60 ksi, and an elongation above approximately 40 percent.

9. A method as recited in claim 8, wherein said stainless steel has an absolute melting temperature, $T_M$, and said first temperature is between approximately $0.4T_M$ and approximately $0.6T_M$.

10. A method as recited in claim 8, wherein said heating step produces sub-grains and fine grains in said stainless steel.

11. A method as recited in claim 8, wherein said stainless steel has less than approximately 0.03 weight percent carbon.

12. A method as recited in claim 11, wherein said stainless steel has less than approximately 0.02 weight percent oxygen, and less than approximately 0.1 weight percent nitrogen.

13. A method as recited in claim 8, wherein said deforming step is accomplished by drawing a tube made of said stainless steel.

14. A method as recited in claim 13, wherein said tube is drawn to a final outside diameter that is less than approximately 0.160 inches.

15. A process for manufacturing a stent assembly having improved mechanical properties, the process comprising the steps of:
providing an oversized tube of an alloy having between approximately 17 and approximately 19 weight percent chromium and between approximately 13 and approximately 15 weight percent nickel;
cold working the oversized tube by drawing to a selected reduced diameter and wall thickness to a yield strength above about 125 ksi; and
heating said cold-worked tube to a temperature between about 45 percent to about 70 percent of the absolute melting temperature of the alloy for a sufficient time, followed by cooling to produce a material having a yield strength between approximately 50 and approximately 60 ksi, and an elongation above approximately 40 percent.

16. The process as recited in claim 15, wherein the temperature is about one-half the absolute melting temperature of the alloy.

17. The process as recited in claim 15, wherein said heating step produces sub-grains and fine grains in the alloy.

18. The process as recited in claim 15, wherein the alloy has less than about 0.03 weight percent carbon.

19. The process as recited in claim 18, wherein the alloy has less than approximately 0.02 weight percent oxygen and less than approximately 0.1 weight percent nitrogen.

20. The process as recited in claim 15, wherein the alloy of the oversized tube is stainless steel.

21. The process as recited in claim 15, wherein the material has more than approximately 200 grains per $10^{-4}$ square inch.

22. A process for manufacturing a stent assembly having improved mechanical properties, the process comprising the steps of:
first, providing an oversized tubular member of an alloy;
second, drawing the oversized tubular member to a smaller outer diameter and thinner wall to the tube to a yield strength above approximately 125 ksi; and
third, heating the cold-worked tube to a first temperature for a sufficient time, followed by cooling to produce a material having a structure with more than approximately 600 grains per $10^{-4}$ square inch.

23. A method for manufacturing a stent, said method comprising the steps of:
deforming a stainless steel having between approximately 17 and approximately 19 weight percent chromium and between approximately 13 and approximately 15 weight percent nickel to a strain in excess of approximately 30 percent; and
heating said deformed stainless steel to a first temperature, followed by cooling to produce a material having a structure with more than approximately 200 grains per $10^{-4}$ square inch.

24. A method for producing a material having improved mechanical properties, said method comprising the steps of:
deforming a stainless steel having between approximately 17 and approximately 19 weight percent chromium and between approximately 13 and approximately 15 weight percent nickel to a strain in excess of approximately 30 percent; and
heating said deformed stainless steel to a first temperature, followed by cooling to produce a material having a yield strength between approximately 50 and approximately 60 ksi, and an elongation above approximately 40 percent,
wherein said deforming step is accomplished by drawing a tube made of said stainless steel.

25. The method as recited in claim 24, wherein said tube is drawn to a final outside diameter that is less than approximately 0.160 inches.

* * * * *